US007001989B2

(12) United States Patent
Church et al.

(10) Patent No.: US 7,001,989 B2
(45) Date of Patent: Feb. 21, 2006

(54) CONJUGATES COMPRISING TWO ACTIVE AGENTS

(75) Inventors: Nicola Jane Church, Kent (GB); Roy Harris, Notts (GB)

(73) Assignee: Elan Drug Delivery Ltd., (GB)

( * ) Notice: Subject to any disclaimer, the term of this patent is extended or adjusted under 35 U.S.C. 154(b) by 299 days.

(21) Appl. No.: 10/302,428

(22) Filed: Nov. 22, 2002

(65) Prior Publication Data

US 2003/0087826 A1 May 8, 2003

Related U.S. Application Data

(63) Continuation of application No. 09/554,424, filed as application No. PCT/GB98/03442 on Nov. 16, 1998, now abandoned.

(30) Foreign Application Priority Data

Nov. 14, 1997 (GB) .................................. 9724143

(51) Int. Cl.
    C07K 1/00      (2006.01)
    C07K 14/00     (2006.01)
    C07K 16/00     (2006.01)
    C07K 17/00     (2006.01)
(52) U.S. Cl. ...................... 530/363; 530/380; 530/382; 530/384; 530/402
(58) Field of Classification Search .............. 530/382, 530/363, 380, 402, 427, 322, 383; 424/193.1, 424/484; 514/2, 18
See application file for complete search history.

(56) References Cited

U.S. PATENT DOCUMENTS

| 4,970,300 A | 11/1990 | Fulton et al. |
| 5,716,614 A | 2/1998 | Katz et al. |
| 5,977,313 A | 11/1999 | Heath et al. |

FOREIGN PATENT DOCUMENTS

| EP | 0278781 | 8/1988 |
| WO | WO 9618388 | 6/1996 |
| WO | WO 9817319 | 4/1998 |
| WO | WO 9639128 | 12/1999 |

OTHER PUBLICATIONS

Colman, R.W. et al. "Hemostasis and Thrombosis. Basic Principles and Clinical Practice" J.B. Lippincott Company, Philadelphia, pp. 29-33 (1993).
Zara, J.J. et al. "A Carbohydrate-Directed Heterobifunctional Cross-Linking Reagent for the Synthesis of Immunoconjugates" *Anal Biochem.*, vol. 194, pp. 156-162 (1991).

*Primary Examiner*—Jon Weber
*Assistant Examiner*—Robert B. Mondesi
(74) *Attorney, Agent, or Firm*—Saliwanchik, Lloyd & Saliwanchik

(57) ABSTRACT

The present invention pertains to a pharmaceutical conjugate comprising an insoluble carrier to which first and second active agents are bound, respectively via a first linker to a first functional group on the carrier and via a second linker to a second functional group on the carrier. For example, fibrinogen and Factor VIII can be independently linked to albumin microcapsules.

7 Claims, 1 Drawing Sheet

CONJUGATES COMPRISING TWO ACTIVE AGENTS

This application is a continuation of application Ser. No. 09/554,424, filed Jul. 20, 2000 ABN; which is a National Stage Application of International Application Number PCT/GB98/03442 filed Nov. 16, 1998 and which claims priority to Great Britain Application No. 9724143.4, filed Nov. 14, 1997.

FIELD OF THE INVENTION

This invention relates to pharmaceutical conjugates, in particular those comprising two active agents, and to their production and use.

BACKGROUND OF THE INVENTION

Pharmaceutical conjugates and their production are described in WO 98/17319. In particular, conjugates of albumin microparticles linked by means of a spacer to a RGD peptide, such as fibrinogen, are described. Their production depends on the presence of functional SH groups on albumin. It is also proposed that Factor VIII may be bound, e.g. as a second active agent, for use in treating haemophilia. Binding may be chemical or by adsorption.

SUMMARY OF THE INVENTION

The present invention is based on the utility of such carriers having further functional groups, such as $NH_2$ and COOH groups present on proteins, to provide a site for linking a different or additional, second active agent. The function of each active agent may be retained after binding to the carrier. The invention is of particular value in connection with active components that cannot readily be adsorbed onto the carrier.

In a particularly preferred embodiment of the invention, respective active agents bound to an albumin microcapsule are fibrinogen and another glycoprotein such as Factor VIII. Such products may have utility because one active agent is effective at the site of action and the other acts as a targeting agent.

The present invention also provides novel conjugates, obtained as intermediates in preparing the products having two bound active agents, in which a glycoprotein such as Factor VIII is bound and the carrier has free SH groups. These conjugates may also have therapeutic utility.

BRIEF DESCRIPTION OF THE DRAWING

An embodiment of the invention is illustrated schematically in the accompanying drawing. The drawing shows four steps which are, respectively: (i) activation with EDC of COOH groups on a microcapsule also having SH groups on its surface; (ii) the use of a dihydrazide reagent (in which the hydrazide groups are separated by "spacer") to provide free hydrazine groups linked to the microcapsule via the spacer; (iii) reaction of Factor VIII (FVIII) with the free hydrazide groups, to give bound Factor VIII; and (iv) using the unreacted SH groups, the binding of fibrinogen (Fb). Step (iv) may be conducted as described in WO 98/17319 or by means of other linkers, as described below.

The product of step (iii) is another aspect of this invention, i.e. containing Factor VIII as the sole active agent. The product of step (iv), comprising Factor VIII and fibrinogen, has utility in the treatment of haemophilia.

DESCRIPTION OF THE INVENTION

Figure 1:
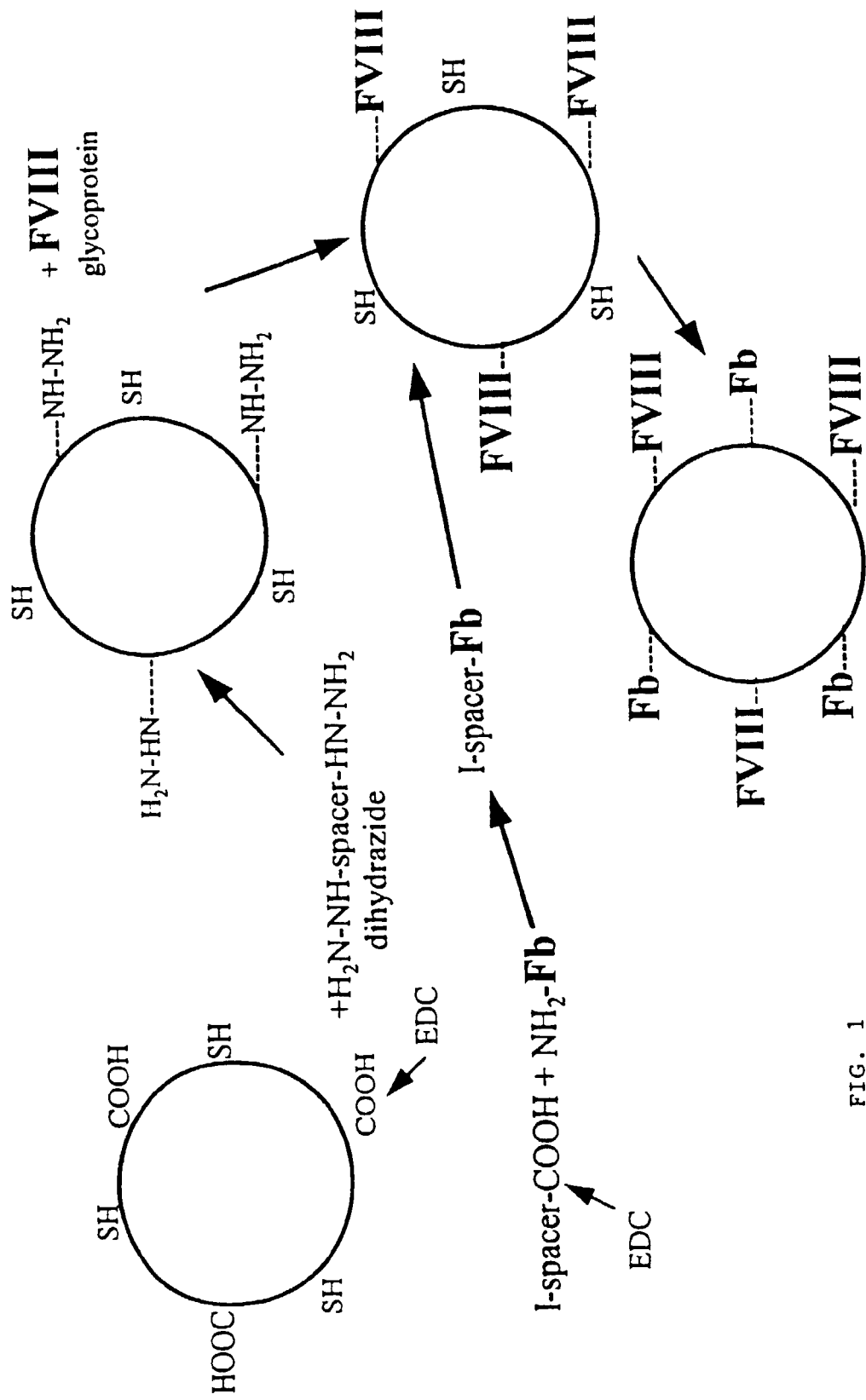

Either or each of the active agents may be a glycoprotein. The first agent is, for example, Factor VIII. Other suitable compounds include Factor IX other blood factors including blood coagulation factors, proteins of the coagulation cascade, thrombolytic agents, antibodies and α-1 antitrypsin.

The second active agent is, for example, fibrinogen. Other suitable compounds are RGD-containing peptides and fibrinogen γ-chains.

The active agent may be a peptide (by which is meant any peptide, polypeptide, protein or conjugate thereof) or include a peptide portion, e.g. a glycoprotein. Such molecules may be linked to microcapsules, via a linker including a spacer. More specifically, the invention utilises the fact that a carrier of a protein such as human serum albumin (HSA) has free carboxyl, amino and thiol groups, with which a bifunctional compound can react. The bifunctional compound preferably has one group selectively reactive with the active component to be conjugated.

In order to retain activity, the respective spacers may be of defined and/or different lengths. Suitable spacer lengths are 10 to 600 nm, e.g. 20 to 400 nm.

The spacer can include enzyme-cleavable peptides, acid or alkali-labile bonds and be of variable length, depending on the requirements of the application. The length of the spacer may be another important aspect of this invention, as it may determine the conjugate's ability to target receptors, such as fibrinogen to GPIIb/IIIa.

By virtue of the invention, controllable cross-linking can be achieved due to the specificity of one of the linking groups for the functional group available on carriers such as HSA. Controllable cross-linking is one important aspect of the present invention, since it may have a direct bearing on the activity of the attached molecule.

This invention provides, inter alia, pure, robust, therapeutically-acceptable, platelet substitutes. Purity may be embodied in the absence of chemical cross-linker and/or surfactant. They are suitable for use in the treatment of thrombocytopenia.

It is an additional feature of the invention that, because fibrinogen acts as a targeting agent, products of the invention may usefully have other bound active agents. Such agents will be chosen with regard to the site of action, usually a wound or other bleeding locus, and to the nature of the problem that is addressed.

By providing a combination of, say, fibrinogen and Factor VIII, the products of the invention may be useful in the treatment of haemophilia. In addition, or as an alternative, to the use of a thrombolytic drug such as urokinase, blood clots may be treated by the use of ultrasound. For this purpose, air-containing microcapsules are especially suitable as the carrier.

The carrier that is used in the invention is preferably produced by spray-drying, under conditions that allow good control of particle size and size distribution. For example, the preferred size is up to 6 μm, e.g. 1 to 4 μm, in order that the particles can pass through capillaries.

Suitable materials and procedures, and also methods for stabilising the microparticles, by heat or by chemical cross-linking, are fully described in WO-A-9218164, WO-A-9615814 and WO-A-9618388, the contents of which are incorporated herein by reference. As explained in the latter publication, the conditions that are described do not affect functional groups, such as the thiol groups in albumin, which therefore remain available for reaction with biological molecules.

The microparticles used in this invention may have the physical characteristics described in the two publications identified above, e.g. being smooth and spherical, and containing air. In order to obtain insoluble, cross-linked microcapsules, the spray-dried product may be reacted with a chemical cross-linking agent. However, heat and γ-irradiation are preferred, and may also sterilise the dry powder products.

A different bifunctional reagent will usually be employed to link the carrier with each active agent. Each bifunctional compound (say, $Y^1$—Y—$Y^2$) that is used in the invention may itself be generated by reaction of simpler compounds $Y^1$—$Y^3$—$Y^4$ and $Y^5$—$Y^6$—$Y^2$, wherein $Y^1$ is specifically reactive with a functional group on the carrier, $Y^4$ and $Y^5$ react together so that $Y^3$ and $Y^6$ together are the spacer Y, and $Y^2$ is the agent-reactive group. For example, $Y^1$ may be thiol-reactive, particularly if $NH_2$ or COOH functional groups have been or are to be used for linking one active agent. As fully described in WO 98/17319, the contents of which are incorporated by reference, $Y^1$ may be I and/or $Y^4$ is COOH, as in $ICH_2COOH$. Such a linker has a free carboxylic acid which can be activated, e.g. using 1-ethyl-3,3-dimethylaminopropylcarbodiimide (EDC), and linked to the amine groups on a peptide. The protein plus linker is then incubated with HSA microcapsules containing free thiol groups.

Fibrinogen may be bound using a conventional bifunctional reagent such as a polyaldehyde. Glycolaldehyde is preferred. Another example of a spacer is sulfosuccinimidyl 4-(iodoacetyl)aminobenzoate (which is water-soluble).

Another linker that may be used is an NHS ester. An NHS ester may be formed by the reaction between a carboxylic acid and N-hydroxysuccinimide in the presence of a carbodiimide. The formation of the active ester must be performed in a non-aqueous environment to prevent hydrolysis of the product. The carbodiimide of choice is therefore the water-insoluble dicyclohexylcarbodiimide (DCC).

Reaction of the active ester with a primary or secondary amine results in the formation of a stable amide bond. The main target functionality for the attachment of the ester to proteins is the α-amino terminus and the ε-amino groups of lysine.

The solubility of NHS esters reflects the conditions in which the compounds are synthesised as they are fairly insoluble in aqueous media. It is often necessary to dissolve the active ester in a solvent before adding to the amine-containing compound. This presents difficulties when adding NHS esters to proteins that do not tolerate high concentrations of solvents. In these cases N-hydroxysulfosuccinimide (sulfo-NHS), a relatively water-soluble alternative to NHS, may be used to create the active ester. Sulfo-NHS esters are quite stable in an aqueous environment and hydrolyse much more slowly than NHS esters.

Further, hydrazide-containing reagents can be used as crosslinkers and will target carbonyl groups on molecules. Aldehyde-containing compounds will react spontaneously with a hydrazide giving rise to a hydrazone linkage. If the compound or protein to be linked to the hydrazone linker does not possess any aldehyde groups, these may be created. Carbohydrate molecules offer the ideal solution and can be converted to aldehydes via a mild periodate oxidation of any cis-hydroxyl groups. Carboxylic acid groups may also be reacted with hydrazide compound, but the reaction requires prior activation of the carboxylic acid by EDC. Proteins contain an abundance of carboxylic acid groups, and the particular amino acid components that would participate in this type of reaction are the side-chains of aspartic and glutamic acid residues.

Another type of linker, typically a heterobifunctional compound, is a maleimide. Maleimides are the product of a reaction between maleic anhydride and either ammonia or a primary amine compound. The double bond of maleimides is capable of reacting with free sulhydryl groups to form stable thioether linkages. The optimum pH for this alkylation reaction is between pH 6.5–7.5.

It may be preferred not to use EDC. For example, a preferred linker comprises the combination of an NHS ester (see above) coupled with a maleimide group. The NHS ester, which would replace EDC, is designed to react with free amine groups producing stable amide bonds without the need for any activation. This covalently attaches, say, fibrinogen to the spacer. The maleimide group, which is highly reactive toward free thiols, reacts specifically with the Cys34 residue on the microcapsules, creating a thioether linkage.

m-Maleimidobenzoyl-N-hydroxysuccinimide ester (MBS) is a commercially available hetero-bifunctional crosslinker that satisfies the requirements for the covalent attachment of fibrinogen to HSA microcapsules in a highly controlled manner. The crosslinker has an NHS ester separated from a maleimide group by benzoic acid. A typical procedure for its use involves the reaction of fibrinogen with MBS to yield the protein as a maleimide activated intermediate.

Purification, e.g. by PEG precipitation, may remove any unreacted MBS before reacting the protein intermediate with the free thiol groups on HSA microcapsules. Current analytical techniques may then be used to determine the activity of the final product.

The loading of fibrinogen or other active agent may be varied using this crosslinking method. The number of free thiols available on the microcapsules for binding may be increased and controlled using 2-iminothiolane (Traut's reagent). Any increase in the number of free thiols would result in an increased number of thioether linkages formed and, therefore, an increased amount of fibrinogen bound.

The hydrazide method of crosslinking may be applied for the attachment of any moiety that possesses a carbohydrate functionality to HSA microcapsules. Specific examples include the γ-chain of fibrinogen, GBIb and Factor VIII.

Another bifunctional linker that may be used is a dihydrazide reagent, e.g. of the formula $H_2N$—NH—$(CH_2)_n$—NH—$NH_2$, wherein n is 4 to 20. In a specific example, n is 6 (adipic acid dihydrazide, or AADH). Appropriate conditions for using it, to provide a bound glycoprotein, will be apparent to those of ordinary skill in the art. This compound will react readily with aldehyde groups and may be coupled to carboxylic acids via the use of carbodiimide activator.

In order to attach the γ-chain of fibrinogen to HSA microcapsules, the carbohydrate clusters located on the γ-chain may have to be subjected to a mild oxidation with sodium periodate. This cleaves the cis-diol component of the sugar ring, to yield reactive aldehydes. If the chain is reacted with AADH the final conjugation of the intermediate to HSA microcapsules may involve the coupling of the free end of the hydrazide linker to the microcapsules' carboxylic acid groups. This may require EDC.

An alternative method of attachment using the hydrazide concept involves a heterobifunctional crosslinker. Such a linker possesses the hydrazide functionality at one end and is separated, e.g. from a pyridyldithio group (S—$SC_5H_4N$), either by a simple carbon chain length, or a more complex aromatic structure. The hydrazide group reacts with aldehyde groups on, say, the periodate-treated γ-chain giving rise to a covalent hydrazone link. The pyridyldithiol group participates in a disulfide exchange reaction with the free thiol, Cys34, on HSA microcapsules.

The carbohydrate attachments which contribute to both the beta and gamma chains within the fibrinogen structure make ideal sites for crosslinking. Each oligosaccharide chain contains eleven monosaccharide units in total, comprising a combination of N-acetylglucose, mannose, galactose and N-acetylneuraminic acid (sialic acid) residues. The carbohydrates are linked through an asparagine residue on both fibrinogen chains.

A crosslinking spacer based on the hydrazide functional group is particularly suitable for the covalent binding of agents such as glycoproteins, e.g. fibrinogen or Factor VIII, to HSA microcapsules. This may be through the carbohydrate moiety, i.e. potentially without affecting the protein portion. As a first step, modification of the terminal sialic acid residue is required. Selective periodate oxidation of the diol present in the sugar side chain results in the formation of an active aldehyde. The sodium periodate concentration and the reaction temperature can be controlled to determine whether sialic acid diols alone are cleaved or whether oxidation is non-selective. Further incubation with a hydrazide functional group results in hydrazone formation. Addition of sodium cyanoborohydride causes reduction and stabilisation of the hydrazone bond, without the need for EDC.

3-(2-pyridyldithio)propionylhydrazide (PDPH) is a preferred crosslinker of this type. It can participate in both hydrazone formation with fibrinogen and a free thiol reaction with HSA microcapsules. The disulphide bond of the hydrazone-derivatised fibrinogen breaks and undergoes a free thiol exchange with the Cys-34 residue on the HSA microcapsules to form a second disulphide bond. This causes the release of pyridyl-2-dithione, the presence of which can be detected by absorbance at 343 nm.

As indicated above, products of the invention containing fibrinogen may act at the site of tumours. Therefore, they may be used in tumour therapy, e.g. by linking a cytotoxic agent by the particular method of this invention or by the methods described in WO-A-9618388. Suitable cytotoxic agents include methotrexate, doxorubicin, cisplatin and 5-fluoro-2-deoxyuridine.

The targeting of drugs to tumour cells may be achieved using products of the invention as vehicles reacting directly with the cells or by participating in the aggregation and deposition of fibrin at the site of cell adhesion.

Products of this invention may be loaded with cytotoxic agents or a combination of cytotoxic and targeting agents. They may then be used to target the disseminated tumour cells in the circulation, by specific interactions with the cell glycoprotein receptors (seek and destroy) or by participation in the platelet aggregation process at the site of adhesion. In both cases, the cytotoxic drug is concentrated at the site of the invading tumour cells.

Alternatively, tumour aggregation may be inhibited in the circulatory system, or even at the site of adhesion, by coating the tumour cell surface with products of the invention, and blocking the sites/mechanisms that activate platelets. This would then allow the body's natural defence mechanisms to facilitate the removal of the tumour cells.

Products containing, for example, the GPIb receptor (interacts with von Willebrands factor) or receptors for collagen or other sub-endothelial matrix components may also be delivered, to potentially block the binding sites for tumour cells by coating the sub-endothelial matrices. The product should still allow an interaction with platelets at the site of a wound, but should also restrict the invasion of vascular wall by any immobilised tumour cell.

An important advantage of the present invention is that the activity of the active agents (or other RGD peptide) can be substantially retained. The content of active fibrinogen can be determined by ELISA; see WO 98/17319.

A conjugate of the invention may comprise at least 0.01%, preferably at least 0.015%, more preferably at least 0.02%, and most preferably at least 0.025%, active glycoprotein. The amount of fibrinogen should not be too great, in order to avoid aggregation, e.g. up to 1, 1.5, 2 or 2.5%. Of the fibrinogen content, it is desirable that at least 50%, preferably at least 70%, more preferably at least 90%, should be active. This can be deterrmined with respect to the total content of fibrinogen, which again can be measured by method such as ELISA. Total fibrinogen may also be determined by radio-labelling, e.g. with $^{125}I$, and counting, by conventional procedures.

The fibrinogen may be blood-derived, transgenic or recombinant, full-length or any active fragment thereof. Fragments are disclosed, inter alia, by Coller et al, J. Clin. Invest. 89:546–555 (1992).

For use as a therapeutic agent, a product of the invention may be administered as is, or mixed with any suitable carrier known to those of ordinary skill in the art. The amount of the product administered will be determined largely to the severity of the wound or other condition to be treated. A typical dosage may be $1.5\times10^9$ microcapsules per kg body weight.

The following Examples illustrate the invention.

HSA microcapsules used in the Examples were prepared by spray-drying and were then stabilised by heating, as described in WO-A-9615814. Two functional groups on the HSA microcapsules were targeted for covalent attachment, namely amine and free thiol moieties. Specific crosslinkers were chosen for both proteins to utilise these different groups.

The fibrinogen used in the Examples was a full-length, blood-derived, commercially available product (SNBTS) that had been doubly virally-inactived.

ALPHANATE® Factor VIII was obtained from Grifols UK and used throughout. Aliquots of 1 international unit Factor VIII/ml in distilled water were stored at −20° C. until required.

Factor VIII was attached using 1-ethyl-1,3-dimethylaminopropyl carbodiimide (EDC) and the homobifunctional spacer, adipic acid dihydrazide (AADH). Activation of the carboxyl groups on the Factor VIII protein is facilitated by reacting with EDC prior to the addition of AADH. The free hydrazide moiety at the remaining end of the crosslinker then reacts with the amine functionalities on the HSA microcapsules, releasing a urea derivative. Fibrinogen was attached using MBS.

The assay used for analysis of Factor VIII loading and activity is the Quadratech Coatest VIII: C/4 Assay kit. The assay utilises the cofactor capabilities of Factor VIII.

The slide test assay records the time taken for the final product to react with thrombin to form aggregates. The final product (50 μl) was placed onto a microscope slide and thrombin (50 μl) added. The two were stirred for 2 seconds and the time from when aggregates begin to form to when the aggregation ends is recorded.

In a repeat experiment, the final product was formulated using 51 mg/ml mannitol, 25 mM sodium phosphate buffer pH 7.0. Sample counts were obtained from the Coulter Multisizer and the volume of formulating agent required to give a sample concentration of 1500 million microcapsules per ml calculated. The sample was centrifuged at 3500 rpm for 2 minutes and the supernatant decanted prior to resuspension in the calculated volume of formulation buffer.

EXAMPLE 1

An aliquot was removed from a 3 mg/ml stock solution of MBS in DMF (8 µl, 24 µg, 72.5 nmoles) and added to 20 mM sodium phosphate pH 7.5 (1867 µl). The solution was mixed thoroughly and fibrinogen (125 µl of 40 mg/ml solution in distilled water, 14.5 nmoles) introduced to make a total reaction volume of 2 ml. The mixture was reacted for 30 minutes at room temperature with continuous stirring.

Microcapsules (100 mg, 1515 nmoles) were sunk in 1% Tween 80 and washed twice in distilled water, once in reaction buffer, 20 mM sodium phosphate pH 7.5, prior to reaction, to remove any excipients.

The fibrinogen solution was then added to the HSA microcapsules and reacted for a further 30 minutes at room temperature. After the product had been washed twice in reaction buffer to remove any excess unreacted fibrinogen, the supernatant was discarded and 1 U FVIII added (1 U FVIII in distilled water). Total reaction volume 1 ml. The HSA microcapsules were sunk in 1% Tween 80 for 30 minutes and washed twice in distilled water and once in 20 mM sodium phosphate buffer pH 7.5 prior to addition to the respective protein sample.

A 0.1 mg/ml stock solution of adipic acid dihydrazide (AADH) was prepared in 20 mM sodium phosphate pH 7.5. An aliquot (12 µl, 1.2 µg) was added to buffer (988 µl) to make a total volume of 1 ml. One unit of Factor VIII was then added.

A 0.02 mg/ml EDC solution in the same buffer was prepared by aliquoting 200 µl of 1 mg/ml solution into 10 ml buffer. EDC (41 µl, 0.82 ng, 5 molar equivalents) was then introduced to the protein solution and reacted for 4 hours at room temperature.

Samples containing derivatised FVIII were reacted in the presence of microcapsules for 4 hours and derivatised fibrinogen samples 30 minutes irrespective of the order of reaction.

After the reaction time between one protein and HSA microcapsules was completed, the sample was washed prior to the addition of the second derivatised protein. When fibrinogen was reacted first, the samples were washed twice in buffer and the supernatant of the final wash decanted before the introduction of derivatised FVIII. When FVIII was reacted first, one washing stage was used.

Controls were included which contained one crosslinked protein and microcapsules. A sample of fibrinogen (5 mg) in 20 mM sodium phosphate buffer (2 ml, 2.5 mg/ml protein concentration) was also put through the Quadratech Coatest assay.

Results obtained from these experiments are shown in Table 1. The concentration values are not corrected by the control samples.

TABLE 1

| Sample | Slide test/ seconds | Formulated slide test/ seconds | Concentration/ µ Units | Yield/% |
|---|---|---|---|---|
| Control 1 | | | | |
| Fibrinogen-MBS + | 1–3 | 2–15 | (0.2331) | (23) |
| microcapsules | 1–4 | 3–8 | (0.1351) | (13) |
| Control 2 | | | | |
| FVIII/AADH/ED | N/A | N/A | 0.2741 | 27 |
| C + microcapsules | N/A | N/A | 0.2589 | 26 |
| Reaction 1 | | | | |
| Fibrinogen-MBS | 1–4 | 5–10 | 0.1718 | 17 |
| first | 2–5 | 7–21 | 0.0765 | 8 |
| Reaction 2 | | | | |
| FVIII/AADH/ED | 3–7 | 11–20 | 0.3311 | 33 |
| C first | 2–4 | 14–26 | 0.3674 | 37 |
| Fibrinogen only | N/A | N/A | 0.1253 | 13 |

The slide test activity of Control 1 was compared with the two reaction samples. It was noted that the addition and reaction of derivatised Factor VIII prior to the introduction of fibrinogen resulted in a decrease in activity. This decrease may be due to a reduced loading of fibrinogen in the presence of crosslinked FVIII. However, when derivatised fibrinogen was reacted firstly with the microcapsules, no significant change in activity was recorded when compared to Control 1.

The low percentage yield of FVIII obtained in Reaction 1 suggests that prior reaction of MBS-fibrinogen with microcapsules appears to obstruct the loading of Factor VIII. This may be a result of excess fibrinogen adsorbing onto the surface of the HSA microcapsules blocking the crosslinking sites.

When Reaction 2 is compared to Control 2, however, the FVIII concentration is increased and this may be due to the impurities, such as Factor VIII, Factor IXa or Factor Xa, in the fibrinogen starting material. These impurities would also account for the positive activity which was recorded in the fibrinogen-MBS control in which no FVIII was present. The fibrinogen only sample also gave a positive result under assay conditions which confirms the presence of impurities interfering with concentration values obtained from the assay.

The results indicate that it is preferable to react FVIII derivatised using AADH and EDC with HSA microcapsules prior to the addition of derivatised fibrinogen to yield a final product which retains high activity of both the proteins.

EXAMPLE 2

The methodology described in Example 1, in which derivatised Factor VIII was reacted prior to addition of derivatised fibrinogen, was followed. A control was included which contained only recombinant fibrinogen reacted with MBS and microcapsules. A sample of recombinant fibrinogen was also assayed. Results are shown in Table 2; they are not corrected by the control values.

TABLE 2

| Sample | Slide Test/ seconds | Formulated slide test/ seconds | Concentration/ $\mu$ Units FVIII | Yield/% |
|---|---|---|---|---|
| Rfibrinogen only Control | N/A | N/A | 0.0354 | 4 |
| Rfibrinogen/MBS + microcapsules only Reaction | 3/4–8 | 16/17–24 | 0.1334 | 13 |
| FVIII/AADH/ EDC first + Rfibrinogen/MBS | 5–9 | 21–34 | 0.3021 | 30 |

Recombinant fibrinogen only resulted in a much smaller concentration value being recorded from the Coatest assay when compared to the SNBTS fibrinogen sample in Example 1. This difference can be explained by the absence of impurities in recombinant fibrinogen. The increase in concentration of the control sample was unexpected and may be due to the HSA microcapsules also having an effect on the assay in the absence of Factor VIII.

The slide test activity was less than for products of Example 1. This loss of activity may be caused by reduced loading of recombinant fibrinogen under the conditions used. It will be evident that modifications may be made, to optimise the final product activity.

We claim:

1. A pharmaceutical conjugate comprising an insoluble carrier to which first and second active agents are bound, respectively via a first linker to a first functional group on the carrier and via a second linker to a second functional group on the carrier, wherein one of the agents is effective to treat said bleeding condition or tumor and the other agent acts as a targeting agent to the site; and wherein the carrier is an insolubilized protein and the functional groups are selected from the group consisting of SH, $NH_2$ and COOH; and wherein one of the agents is a glycoprotein.

2. The conjugate according to claim 1, wherein the carrier is insolubilized human serum albumin.

3. The conjugate according to claim 1, wherein the carrier is in the form of microcapsules.

4. The conjugate according to claim 1, wherein the first agent is Factor VIII.

5. The conjugate according to claim 1, wherein the second agent is fibrinogen.

6. The conjugate according to claim 1, wherein the first linker is at least 10 nm long.

7. The conjugate according to claim 1, wherein the first linker is a dihydrazide reagent.

* * * * *